United States Patent [19]
Mirowski et al.

[11] 3,942,536
[45] Mar. 9, 1976

[54] CARDIOVERTING DEVICE HAVING SINGLE INTRAVASCULAR CATHETER ELECTRODE SYSTEM AND METHOD FOR ITS USE

[75] Inventors: Mieczyslaw Mirowski, Owings Mills; Morton M. Mower, Baltimore, both of Md.; Rollin H. Denniston, III, Anoka, Minn.

[73] Assignee: Mieczyslaw Mirowski, Owings Mills, Md.

[22] Filed: Sept. 19, 1973

[21] Appl. No.: 398,793

Related U.S. Application Data

[63] Continuation-in-part of Ser. No. 124,326, March 15, 1971, abandoned.

[52] U.S. Cl. ............................. 128/419 D; 128/404
[51] Int. Cl.$^2$ ........................................ A61N 1/36
[58] Field of Search ..... 128/2.05 R, 2.06 E, 2.06 R, 128/404, 419 D, 419 P, 419 R, 421, 423, 205 D, 205 P

[56] References Cited
UNITED STATES PATENTS 3,614,954  10/1971  Mirowski et al. ............... 128/419 D
3,738,370  6/1973  Charms ........................... 128/419 D

OTHER PUBLICATIONS

Rogel et al., "Journal of Thoracic & Cardiovascular Surgery," Vol. 61, No. 3, Mar. 1971, pp. 466–471.

*Primary Examiner*—William E. Kamm
*Attorney, Agent, or Firm*—Fleit & Jacobson

[57] ABSTRACT

Apparatus and method for either manually or automatically initiating the cardioversion of a malfunctioning heart. The apparatus includes a single intravascular catheter electrode system which allows for a much more compact cardioverting system capable of being completely implanted within the patient. The heart function is continuously monitored, and when the function becomes abnormal, the malfunctioning heart is shocked by a voltage of sufficient amplitude to restore the heart to normalcy. If the heart does not return to its normal functions after a given interval, then it is again shocked. Normal heart activity ensures that the shocking mechanism remains inert.

42 Claims, 5 Drawing Figures

FIG. 1

INVENTORS
MIECZYSLAW MIROWSKI
MORTON M. MOWER
ROLLIN H. DENNISTON III
BY Irving S. Rappaport

FIG. 2

RIGHT VENTRICULAR PRESSURE CURVE

CARDIOVERTING DEVICE HAVING SINGLE INTRAVASCULAR CATHETER ELECTRODE SYSTEM AND METHOD FOR ITS USE

RELATED APPLICATIONS

This is a continuation-in-part of U.S. Pat. Application Ser. No. 124,326 filed Mar. 15, 1971, now abandoned.

BACKGROUND OF THE INVENTION

During the past several decades, coronary heart disease has come to occupy the first position among the causes of death in the developed areas of the world. In the United States, for example, this disease is responsible for over one-half million deaths yearly. And of this number, more than half occur suddenly, outside the hospital, and therefore before the patient is able to obtain the necessary medical assistance. Although the precise cause of sudden death in coronary heart disease has not yet been entirely clarified, the available evidence permits the medical field to ascribe death in the majority of these cases to grave disturbances in cardiac electrical activity culminating in ventricular fibrillation.

The frustrating but related problem is the present inability to deal effectively with lethal and non-lethal arrhythmias outside of a hospital setting. Within the hospital environment, recent experience has clearly demonstrated that ventricular fibrillation and its frequent precursor, ventricular tachycardia, are reversible phenomena when prompt defibrillation of the heart is instituted. Under such circumstances, cardiac function can frequently be restored to normal without the patient suffering from residual disability. Unfortunately, however, the state of the art makes defibrillation very much dependent upon a highly specialized medical environment, thus limiting such treatment to elaborately equipped modern hospitals.

There is no question that a great need exists for a defibrillator which could be carried by those who are prone to having one of the many life threatening arrhythmias generally discussed above. Thus, in some patients having coronary heart disease, a fatal outcome from ventricular tachycardia or ventricular fibrillation could be avoided, even in the absence of immediate medical assistance. The first step, of course, is the detection of those prone to suffering from cardiac malfunctions leading to ventricular tachycardia or ventricular fibrillation.

While it is not possible to predict with unerring certainty which patients suffering from coronary heart disease will be the victims of sudden death, several high risk groups of patients can be recognized. For example, patients who have experienced myocardial infarction, even though they may be surviving in good health, run a substantial risk of dying suddenly, a risk several times greater than that associated with the general population. Further, if patients with myocardial infarction have a history of serious ventricular arrhythmias and/or of cardiac arrest, or if evidence of persistent myocardial irritability is present, it may logically be assumed that the risk of sudden death is increased substantially. Patients like those described above would greatly benefit from an automatic, standby or demand defibrillator.

Also, such an automatic defibrillator would be an asset to those hospitalized patients who have suffered myocardial infarction both in the coronary care unit and those who have been discharged from the well-equipped coronary care unit. Under such circumstances, the defibrillator could be utilized temporarily for the remainder of the expected hospital stay; or the automatic defibrillator could be permanently implanted for use both in the hospital and after discharge.

Another recognizable class of patients particularly in need of an automatic defibrillator is the class composed of those who have not shown prior histories of myocardial infarction but who show severe symptoms of coronary heart disease, such as ventricular arrhythmias resistant to medical treatment or angina pectoris.

From the brief discussion above, there should be little doubt that the possible applications for an automatic defibrillator are numerous. Such automatic standby defibrillators have been developed and are described in U.S. Pat. No. Re. 27,757 entitled STANDBY DEFIBRILLATOR AND METHOD OF OPERATION and U.S. Pat. No. Re. 27,652 entitled ELECTRONIC STANDBY DEFIBRILLATOR.

The automatic standby defibrillators described in the above-identified patents employ a sensing probe carrying one electrode which is positioned in the right ventricle of the heart. A second electrode, separate from and unconnected to the sensing probe, is generally a flat plate either placed on the outer surface of the chest, sutured under the skin of the anterior chest wall or applied directly to the ventricular myocardium. As a result, these systems require much more surgery and, depending on the position of the second electrode, may ultimately be only partially implanted. In addition, such systems require a capacitor of sufficient size and capacity to store approximately several hundreds of watt-seconds, which is the necessary energy required in those systems to produce defibrillation. Therefore, it is evident that an automatic standby or even a manually initiated defibrillating system which requires a much lower energy level, thereby being much smaller and compact in size and which may be totally and completely implanted within the patient, would be highly desirable and would represent a great improvement.

Another drawback of the prior art relates to the possibility of developing ventricular fibrillation in the course of correcting, for example, atrial fibrillation. In the prior art, the heart is often brought out of artial fibrillation by delivering an electrical shock across the chest by means of precordial electrodes, or paddles. With such an arrangement, it is necessary to develop a large electrical potential across the paddles, but impossible to centralize the potential across the atria. Accordingly, it is essential to very carefully time the pulses delivered to bring a malfunctioning heart out of atrial fibrillation, or the large shock across the ventricles may induce ventricular fibrillation. This is yet another indication of the need for a low-energy intravascular electrode system capable of accurately delivering electrical pulses to localized areas of the heart.

Two other disadvantages of the prior art high-energy cardioverting systems, and the need for improvement, should be noted. First, because of the extreme pain which could be experienced by a patient undergoing high-energy cardioversion, it is the practice to administer a general anesthetic before an attempted cardioversion. With a low-energy intravascular electrode system, the use of a general anesthetic can be avoided.

Secondly, the application of high-energy electrical shocks across the chest of a patient carries with it substantial risk of cardiac damage. Again, by way of a low-energy intravascular electrode system capable of localizing defibrillating electrical shocks, the potential risk of injuring the myocardium is considerably decreased.

In this regard, efforts have been made to experiment with defibrillators other than that described above. For one, see Hopps et al., "Electrical Treatment of Cardiac Arrest: A Cardiac Stimulator-Defibrillator," Surgery, Vol. 36, No. 4 (Oct. 1954), at pages 833–849. There, the researchers attempted to bring dogs out of ventricular fibrillation by using an intracardiac electrode carrying two very closely spaced electrodes. The authors concluded that shocks applied through an intracardiac catheter were not effective in cardiac defibrillation. A second example can be seen in recently issued U.S. Pat. No. 3,738,370. There, a single catheter carries a pair of electrodes spaced together so closely as to allow placement of both electrodes in the atrium. Though the patentee alleges effective cardioversion, the energy levels are higher than are actually necessary. The electrode spacing and location are seen to be the reasons. Therefore, to date, the medical field is without a simple, low-energy cardioverting device using a single intravascular electrode catheter capable of treating a wide range of atrial and ventricular arrythmias.

SUMMARY OF THE INVENTION

The present invention relates to just such a cardioverting device. As used herein, a cardioverter is an electronic system which, after detecting one of the above-noted lethal or non-lethal arrhythmias, reestablishes normal heart function in the heart of the user. "Cardioverting" or "cardioversion" as used herein is intended to encompass the correction of a number of arrhythmic heart conditions, both lethal and non-lethal. Those arrhythmic heart conditions include atrial tachycardia, atrial flutter, atrial fibrillation, junctional rhythms, ventricular tachycardia, ventricular flutter, and ventricular fibrillation, and any other non-pacemaking related arrhythmic condition which may be corrected by applying electrical shocks to the heart. Obviously then, "defibrillation" is included in the term cardioversion as a method of applying electrical shocks to the heart to defibrillate fibrillating atria or fibrillating ventricles.

The system of the present invention may be installed in patients particularly prone to develop ventricular tachycardia and/or ventricular fibrillation, or other types of tachyarrhythmias which may be corrected by cardioverting, either on a temporary or a permanent basis. And, because of extremely small and compact size, the system including both electrodes may be totally and completely implanted under the skin of the patient, or alternatively, may be carried externally, save for the sensing probe carrying the two electrodes.

More particularly, the present invention relates to a device for reliably sensing the differences between a properly functioning heart and one which has suddenly developed an arrhythmia correctable by cardioverting, and for then delivering a cardioverting shock to the arrhythmic heart. The device is adapted to continue delivering intermittent shocks to the heart in the event that the heart fails to return to its normal behavior pattern, and has the ability of automatically regaining sensing control over a functional heart thereby ensuring that further shocks are inhibited after successful cardioversion has taken place.

The standby defibrillator of the present invention has as its basic element, a capacitor capable of storing electrical energy in an amount sufficient to cardiovert a malfunctioning human heart. Upon discharge of this capacitor, a shock is delivered to the heart through the two stimulating electrodes. A sensing probe carries both electrodes, the whole unit forming a single intravascular catheter electrode system. One electrode forms the distal tip of the intracardiac catheter and is positioned within the right ventricle (when dealing with a ventricular arrhythmia) while the second stimulating electrode is spaced from the first electrode and is positioned either within the heart or in the vascular system outside the heart.

The capacitor is associated with a sensing circuit connected to the proximal end of the intracardiac catheter and is adapted to respond to a signal recorded at the distal end of the catheter. The signal sensed by the catheter must, of course, be inherently related to some distinctive characteristic of ventricular tachycardia or ventricular fibrillation; and in a specific embodiment of the present invention, the pressure in the right ventricle is sensed. When this pressure falls below a given value, on the order of 5 to 15 mm hg, the heart is malfunctioning and, therefore, the capacitor is discharged into the heart.

Between the sensing circuit and the capacitor, means are provided for delaying the repetition of depolarizing discharges for a preset period of time (on the order of 10 to 30 seconds). This delay is essential to give the heart the opportunity to be converter spontaneously to a normal cardiac rhythm, and also to ensure that the abnormal heart conditions are, in face, critical. Only in the absence of a successful conversion is a subsequent shock delivered to the heart. In a particular embodiment of the present invention, the time delay is brought about with the aid of a sawtooth generator, a relay and the charge time of the storage capacitor.

The above discussion, for the most part, has been directed to ventricular arrhythmias. It should be remembered, however, that the present invention is also well suited to treat arrhythmias of the atria. When being used in such a mode of operation, one electrode of the catheter is positioned in the right atrium while the other electrode resets outside the heart.

Accordingly, an aspect of the present invention is to provide either a manual or an automatic standby cardioverting device having a single intravascular catheter electrode system.

Another feature of the present invention is the provision of either a manual or an automatic standby cardioverting device capable of defibrillating a malfunctioning heart extremely rapidly and at relatively low energy levels. This device is extremely compact and includes an electrode system which is totally and completely implantable in the body of a patient. The unit lies dormant during normal heart activity but applies a shock to the heart when the heart functions become abnormal. If the unit is automatic, it reliably senses the difference between a normally functioning heat and one which has suddenly developed abnormal function, and then automatically delivers a cardioverting shock to the heart. Further, the unit is capable of delivering multiple shocks in the event that the heart is not successfully cardioverted by the initial shock; and is designed to automatically regain sensing control over a functioning heart, thereby inhibiting further shocks after successful cardioversion. Still another feature of the present invention is that it may sense conditions requiring either cardioversion or pacing.

The particular design of the intravenous catheter is an important aspect of the present invention. First, it is important that the catheter be flexible. Otherwise, the catheter could not safely be inserted and positioned in the heart. Second, it is important that the electrodes on the catheter have a sufficient contact surface so as to effectively discharge the stored energy through the heart. Thirdly, the electrode placement in the heart and, hence, the spacing between the distal and proximal electrodes on the catheter, are important to the effectiveness of the device. In the preferred embodiment of the invention, the intravascular catheter includes at least two spaced electrodes for discharging energy into the heart, with the electrode spacing being such that when the distal electrode is located in the heart cavity undergoing the arrythmia to be cardioverted, the proximal electrode lies outside the heart.

Based upon the foregoing preferred criteria, and in light of the well-known average heart sizes, the electrode spacing can be determined. For example, in the average adult, the heart measures about 12½ cm. from the base to the apex. On the other hand, the length of the right ventricular inflow tract, that is, the internal spacing between the tricuspid annulus and the apex, is approximately 7½ cm. Thus, taking into consideration the average thickness of the ventricles, the spacing between the base of the right atrium and the superior vena cava is approximately 3½ cm. See, for example, S. E. Gould, *Pathology of the Heart*, 2d. Ed., Charles C. Thomas, publisher, p. 95; and S. A. O. Eckner, et al., "Dimensions of Normal Human Hearts," *Archives of Pathology*, vol. 88 (1969), pp. 497–507.

While it is preferable that an electrode be tailored to the user, based upon his precise heart measurements, useful ranges of electrode spacings can be set out for commercial production.

For ventricular cardioversion, the most adjacent distal and proximal electrodes are spaced at least two and one-half to three inches apart. As a practical range, the electrodes would be spaced apart somewhere between two and one-half and six inches apart. More preferably, the spacing would be between three and five inches, and for commercial exploitation, would be between 4 and 4½ inches. For atrial cardioversion, on the other hand, the electrodes would be spaced at least 2½ to 3 inches apart, with the maximum electrode spacing again being somewhere between 2½ and 6 inches, and in the commercial embodiment, would be spaced apart somewhere from between 2½ and 4 inches.

These and other aspects of the invention, as well as many of the attendant advantages thereof, will become more readily apparent when reference is made to the following description taken in conjunction with the accompanying drawings.

DESCRIPTION OF THE PREFERRED EMBODIMENT

For purposes of description, the present invention will be explained for use in accomplishing ventricular defibrillation. However, it should be understood that the present invention could be employed for performing cardioversions with respect to other arrythmic conditions as described above.

Figure 1:
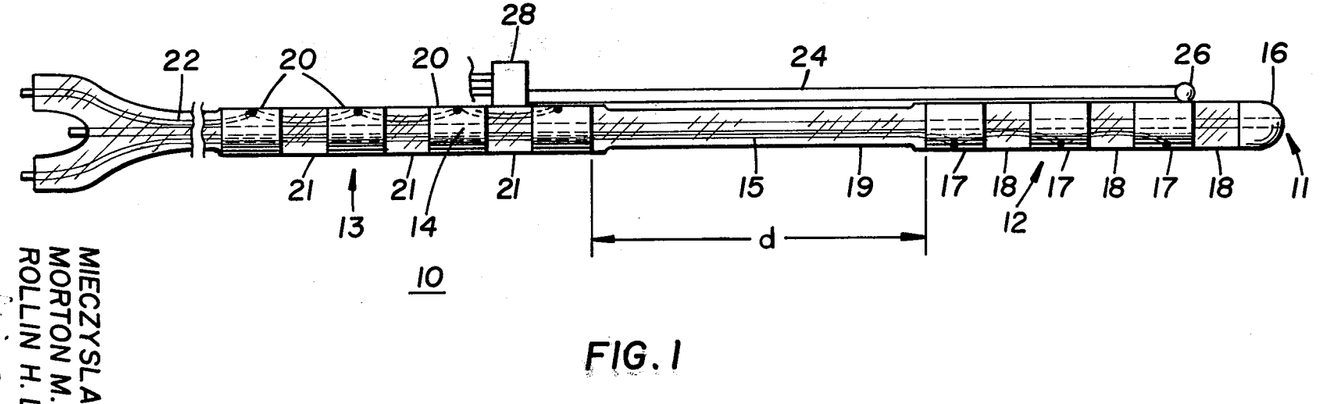
FIG. 1 is a side view of the combination sensing probe and electrode structures defining the single intravascular catheter electrode system which forms a part of the present invention.

FIG. 1 shows a single intravascular catheter electrode system 10 which comprises a pacing tip shown generally at 11, a distal electrode shown generally at 12, and a proximal electrode indicated generally at 13. The term "catheter" as used herein is intended to mean an intravascular or transvenous lead either with or without a lumen. The electrode system 10 is designed so that it is protected from the corrosive environment inside the human vascular system, and is sealed so as to be inert to body fluids. Electrical connection is made via a coil spring wire 14, which is completely molded in a silicone rubber, substantially cylindrical casing 15, and which associates with a hollow conductive cap 16 affixed to the extreme distal end of catheter system 10. Cap 16 serves as the electrodes or pacing tip if it is desired to use the catheter system in a pacemaking mode. A coil spring is used so that a stylet may be passed therethrough to facilitate placement of the catheter system into proper position. Cap 16 may, for example, be made of solid platinum irridium.

Distal electrode 12 comprises a plurality of spaced, conductive metal rings 17, three being shown in the illustrated embodiment. Metal rings 17 may, for example, be made of solid platinum irridium and fit snugly to prevent lateral movement around casing 15. A spacing 18 is left between adjacent rings 17 in order to provide the electrode with the necessary flexibility for positioning in the vascular system without undue stress and strain. A plurality of rings define electrode 12 to provide sufficient surface area and hence good electrical contact with the heart tissues when the catheter is implanted. All of the rings 17 are electrically connected together in series by a low impedance wire 19. Wire 19 may, for example, be platinum tinsel wire or three serve copper tinsel wire. The wire should be sufficiently conductive to adequately deliver the voltage levels used in defibrillating.

Proximal electrode 13 comprises a plurality of spaced-apart conductive metal rings 20, with four being illustrated in the FIG. 1 embodiment. Metal rings 20 may, for example, be made of solid platinum irridium and fit snugly about the molded silicone rubber casing 15. A spacing 21 is left between adjacent rings 20 in order to provide the electrode with the necessary flexibility for positioning in the vascular system without undue stress and strain. A plurality of rings define electrode 13 to provide sufficient surface and good electrical contact with the heart tissues when the catheter is implanted. All of the rings 20 are elecrically connected together is series by a low impedance wire 22. Wire 22 may, for example, be platinum tinsel wire or three serve copper tinsel wire. The wire should be sufficiently conductive to adequately deliver the voltage levels used in defibrillating. Casing 15 seals wires 14, 19 and 22 so as to make them inert from body fluids as well as electrically insulates them from one another.

Although the embodiment shown depicts the distal electrode 12 as having three conductive rings 17 and the proximal electrode 13 as having four conductive rings 20, the number of rings of each electrode may be varied. Also the length of each of the rings 17 and 20, as well as the spacings 18 and 21 respectively between them, may vary. The important relationship is that catheter system 10 be sufficiently flexible to be easily positioned within the vascular system, and at the same time have sufficient surface area on each of the electrodes to provide good electrical contact with the heart when catheter system 10 is properly positioned to deliver energy sufficient to cardiovert the heart. In the specific embodiment shown, rings 17 and 20 are each ¼ inch in length and spacings 18 and 21 are each 3/8 inch. the overall length of catheter system 10 may typically be approximately 60 to 70 cm.

Another dimension of importance is the interelectrode distance, d, shown in FIG. 1 between the distal electrode ring 17 farthest from cap 16 and the closest proximal electrode ring 20 thereto. Of course, the required distance will be slightly different from one patient to the next. However, a good average for ventricular cardioversion is between four and four and one-half inches for the interelectrode distance, d. For atrial cardioversion, the distance, d, would be somewhere between 2½ and 4 inches for the preferred embodiment.

A sensing probe 23 may be carried by catheter system 10 if it is used as an element of an automatic cardioverter. The sensing probe comprises a main body portion 24 and, for example, a pressure sensitive bulb 26. Electrical connections to bulb 26 are made at junction box 28. The main body 24 of the sensing probe is in the shape of a flat ribbon, and the body of bulb 26 is spherical.

Figure 2:
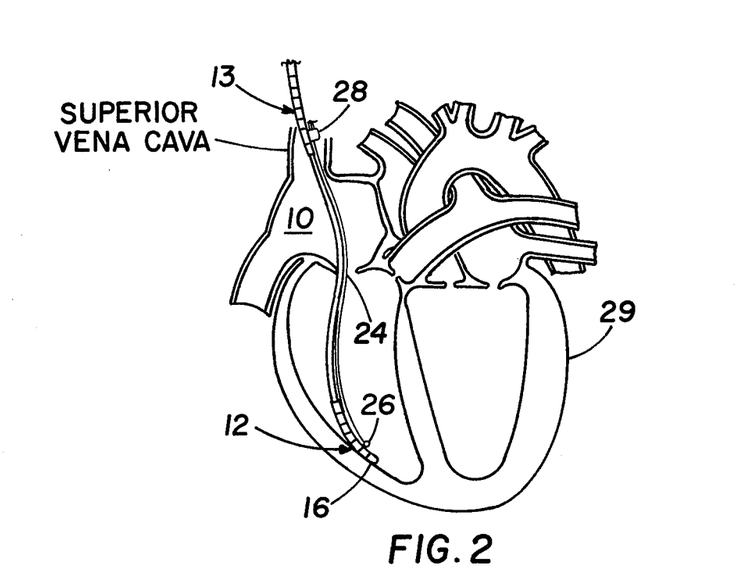
FIG. 2 indicates the catheter system of the present invention positioned in the heart.

FIG. 2 shows one possible position of catheter electrode system 10 in a heart for effecting ventricular defibrillation. Catheter system 10 is introduced through a peripheral vein, such as, for example, the right jugular vein, by means of surgery very similar to that involved in the implantation of a pacemaking catheter. One very effective position has been found to be where the distal electrode 12 is wedged in the apex of the right ventricle and proximal electrode 13 is immediately superior to the right atrium or just outside the cardiac silhouette in the vascular system. In this position distal electrode ring 17 farthest from cap 16 should not be too close to the tricuspid valve and the proper intro-electrode distance, d, should be provided so that proximal electrode 13 lies just outside the cardiac silhouette.

When the catheter system 10 is being inserted in proper position as shown in FIG. 2, cap 16 of pacing tip 11 and electrode 12 are electrically isolated from one another. At this time, therefore, conventional pacemaking signals may be applied between cap 16 and electrode 12 by delivering the appropriate pacemaking signals to coil spring 14 and wire 19, respectively. Since the heart responds favorably to the pacemaking signals only if cap 16 of pacing tip 11 is properly positioned, this method is suitable for checking the position of catheter system 10. The proper location may, of course, be recognized by other methods such as, for example, fluoroscopy or pressure recordings. Once it is determined that catheter system 10 is properly located, it is secured in place and the pacemaking electronics, if unnecessary for the particular patient, are disconnected. The electronic circuit associated with the standby defibrillator of the present invention is then connected to electrodes 12 and 12 via wires 19 and 22, respectively.

Figure 3:
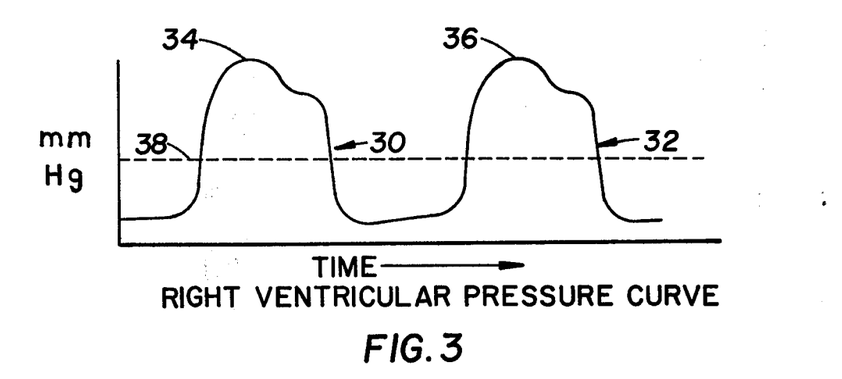
FIG. 3 illustrates a typical pressure curve for the right ventricle of a normally functioning heart.

With reference now to FIG. 3, there is illustrated a right ventricular pressure curve for a normally functioning heart. Only pulses 30 and 32 are illustrated for ease of description, though such pulses repeat at the rate of approximately 60 to 70 per minute in a normally functioning heart. FIG. 3 clearly shows that each pulse has a peak and that these peaks rise above a preset pressure indicated by the dotted line 38. This dotted line corresponds to the threshold between a healthy heart and one which is in need of cardioversion. When the height of the peaks 34 and 36 falls below the pressure indicated by line 38, the malfunction is sensed by probe 23 which, as will be described immediately below, initiates the cardioversion of the heart.

Figure 4:
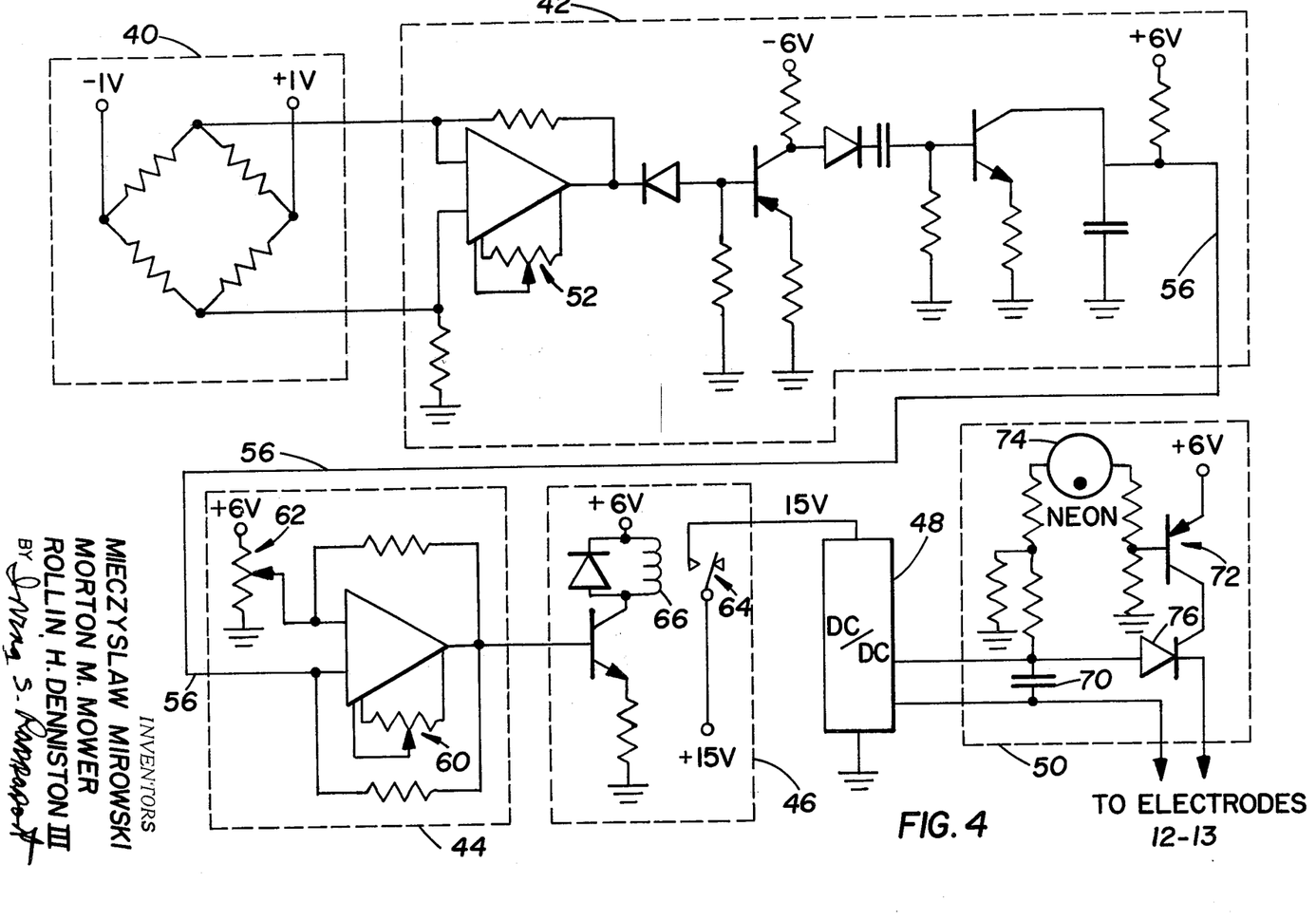
FIG. 4 is a circuit schematic of one embodiment of an electronic circuit which may be employed in the standby defibrillator of the present invention.

With reference then to FIG. 4, one embodiment of an electronic circuit which may be used with the standby defibrillator of the present invention will be described. The electronic circuitry of FIG. 4 may conveniently be broken down into several component parts. The first part is a pressure transducer shown at 40, this pressure transducer being directly associated with the pressure sensing probe 23. The next stage of the electronics is a combination of an amplifier and a sawtooth generator shown at block 42. The amplifier is adapted to amplify the signals received from pressure transducer 40. The sawtooth generator comprises a transistor and a capacitor connected between the collector electrode of the transistor and ground. The signal from the sawtooth generator is then passed to an output amplifier shown at 44, which amplifier in turn feeds its output signal to the base of a transistor associated with the relay stage shown at 46. The relay 46 is normally in its open state condition, but when it is closed, a DC signal is impressed upon a DC/DC converter stage 48. The DC/DC converter 48 boosts the input voltage from approximately 15 volts to the necessary defibrillating voltage. The DC voltage signal from the converter 48 is then fed to a storage capacitor 70 which is associated with a firing circuit, the entire combination shown at 50. When the firing circuit 50 triggers the discharge of the capacitor 70, the necessary defibrillating voltage signal is applied to the electrodes 12 and 13 illustrated in FIG. 1. Therefore, when the sensing probe 23 senses a malfunction in the heart, the capacitor, after a predetermined time delay, shocks the heart with the appropriate defibrillating voltage.

Still referring to FIG. 4, but in greater detail, the circuitry associated with the present invention functions as follows. The pressure transducer 40 takes the form of a resistive bridge, one resistor of which is defined by the pressure sensor 26 on the tip of the probe 23. The remaining legs in the bridge are defined by resistors housed in the junction box 28 shown in FIG. 1. The pressure transducer 40 is arranged so that the pressure sensed by element 26 is converted to an electrical signal, the amplitude of which is directly proportional to the sensed pressure. The output from the pressure transducer 40 is fed to a conventional multistage amplifier shown in block 42 which amplifies the received pulses and which then feeds these amplified pulses to the sawtooth generator also in block 42. The trimming potentiometer 52 is provided to balance the inputs to the associated amplifier.

Figure 5:
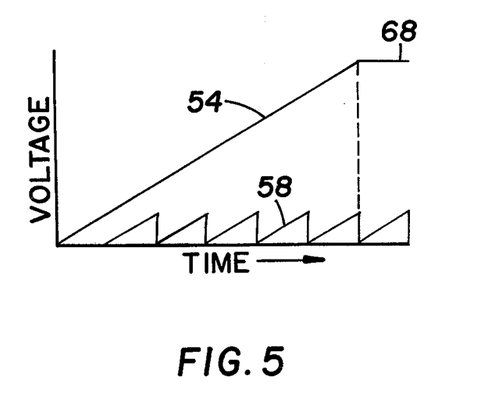
FIG. 5 is a graph of voltage versus time illustrating the operation of the sawtooth generator forming a part of the present invention.

With reference now to FIGS. 3 through 5, the operation of the sawtooth generator will be described. the sawtooth generator, if unaffected by the external environment, will have an output curve such as that shown at 54 in FIG. 5. However, if a signal is fed to the sawtooth generator, and if the signal is at least of a predetermined amplitude, then the output voltage of the generator on lead 56 will immediately drop to zero and then again begin to climb. Therefore, if the sawtooth generator receives repetitious pulses of at least the predetermined voltage, then its output will be similar to that shown in FIG. 5 by waveform 58.

If the heart functions sensed by the pressure transducer 40 are normal, following the curve shown in FIG. 3, then the amplified signal corresponding to a pulse in ventricular pressure will cause the output of the sawtooth generator to drop to zero. The threshold signal reaching the sawtooth generator can be adjusted by adjusting the amplification factor of the signal amplifier shown in block 42. Amplifier 44 has a threshold which is adjusted by potentiometer 62 so that the amplifier 44 actuates the relay 64 only after approximately 6 seconds of heart malfunction. If, then, the ventricular pressure falls lower than that value indicated by the dotted line 38, and so remains for the preset time interval, the amplified voltage reaching the generator will be insufficient to cause the generator output to drop to zero. Rather, the generator output will follow the curve shown at 54 in FIG. 5, and the threshold of amplifier 44 will be reached. Trimming potentiometer 60 is provided to balance the inputs to the associated output amplifier 44 from lead 56 and potentiometer 62.

The output from the amplifier 44 is fed to the relay circuit 46. The relay contacts shown generally at 64 are initially set in the open-circuit condition, thereby isolating the 15 volt source from the DC/DC converter 48. Further, the relay 46 is set to close only after the current passing though coil 66 reaches a predetermined value. With reference to FIG. 5, the voltage output of the sawtooth generator must be at the level 68, the threshold of amplifier 44, before the current in the coil 66 is sufficient to switch the relay 64 into its closed-circuit state.

When the relay 64 closes, then the 15 volt source is connected directly to the DC/DC converter 48. From FIGS. 3 through 5, it can be seen that approximately six seconds must elapse, with the heart continuously malfunctioning, before the relay 64 switches from its open-circuit mode to its closed-circuit mode. This will be apparent when one realizes that each "tooth" of the curve 58 corresponds to one peak of the right ventricular pressure response and, as noted above, the peaks of the pressure curve repeat at approximately 60 to 70 per minute. Therefore, absence of a coordinated ECG-ventricular pressure peak must exist for approximately six seconds before input voltage is fed to the DC/DC converter 48. If the heart returns to its normal function at any time during that 6 seconds, then the sawtooth generator output response would drop to zero and the six second cycle would begin again.

With the relay 64 closed and a 15 volt or other DC signal appropriate from implantable battery sources being impressed upon the converter 48, an output of sufficient voltage to produce defibrillation appears at the output terminals of the converter 48 when capacitor 70 is fully charged. Simultaneously, this voltage signal is fed to a resistive chain and finally to the base of transistor 72 via a neon tube 74. A silicon controlled rectifier (SCR) 76 is triggered on when transistor 72 becomes conductive.

The operation of the firing circuit 50 is as follows: the voltage signal from the converter 48 is fed to the capacitor 70. When the capacitor 70 is fully charged, the transistor 72 becomes conductive, due to the now-conducting neon tube 74. The resistor chains and the tube 74 are interconnected in such a manner that when the voltage across the capacitor 70 reaches the full voltage level from converter 48, then the tube 74 becomes conductive. When the tube 74 conducts, so too does transistor 72 and, therefore, SCR 76. Then, the full defibrillating voltage passes through electrodes 12 and 13 thus shocking the heart with a voltage sufficient to cause defibrillation.

As noted above, it is important that a time period elapse between the detection of a heart malfunction and the delivery of the defibrillating shock to the heart. As also noted above, an approximately 6 second delay occurs between the first detection of a malfunction and the closing of relay 64. Then, there is an additional delay, on the order of a few more seconds, which is brought about by the charge time of capacitor 70. That is, when the relay 64 closes, 6 seconds after the initial malfunction, the capacitor first begins to charge. Preferably, less than 20 seconds elapse between the initial sensing of heart fibrillation and the discharge of the capacitor into the heart. Naturally by varying the rise time of the sawtooth generator and the charge time of the capacitor, the twenty seconds may be enlarged or contracted as desired. And, as mentioned above, if at any time during the delay period the heart returns to normal, then the delay period automatically begins again.

In recent animal experiments using dogs in which fibrillation was induced by an alternating current electrical signal, defibrillation was achieved successfully in less than 3 watt-seconds at voltages as low as a few hundred volts. Even more recently, success in atrial cardioversion was achieved at an energy level of a mere 0.1 watt-seconds. However, it is possible that effective results at lower energies may be achieved by appropriate selection of the system's parameters.

Above, a specific embodiment of the present invention has been described. It should be understood, however, that this description is given for illustrative purposes only and that many alterations and modifications may be practiced without departing from the spirit and scope of the invention. Just as a few examples, it should be understood that while in the specific embodiment of the present invention, the pressure in the right ventricle is sensed as an indication of heart malfunction, other sensing arrangements may be practiced. Further, a single SCR is used as a triggering device. It is possible to substitute this device for a plurality of SCR units or, alternatively, with a vacuum relay. Still further, while the above description shows a single storage capacitor, a series of capacitors could be employed. It is, therefore, the intent that the present invention not be limited to the above but be limited only as defined in the appended claims.

What is claimed is:

1. A method for cardioverting a malfunctioning heart with a single intravascular catheter carrying first and second spaced electrodes for delivering to the heart electrical energy to cardiovert the same, the method comprising the steps of: positioning the single intravascular catheter into association with the heart with said first electrode located within the heart chamber to be cardioverted and said second electrode located outside said heart chamber; sensing heart activityl; and delivering cardioverting electrical energy to the heart across said first and second electrodes when a manfunction susceptible to conversion by electrical shock is sensed.

2. The method of claim 1, wherein said first and second electrodes are spaced apart a distance of at least about 2½ inches.

3. The method of claim 2, wherein said first and second electrodes are spaced apart a distance of between about 3 and 5 inches.

4. The method of claim 3, wherein said first and second electrodes are spaced apart a distance of between about 4 and 4½ inches.

5. The method of claim 2, wherein said first and second electrodes are spaced apart a distance of between about 2½ and 4 inches.

6. The method of claim 1, wherein the cardioverting electrical energy is of at least approximately 0.1 watt-seconds.

7. The method of claim 1, wherein said single intravascular catheter is flexible for safe passage through the venous system, and wherein said electrodes are ring shaped.

8. The method of claim 1, and further comprising the step of: delaying the delivery of energy to the heart for a predetermined time after sensing a malfunction.

9. The method of claim 1, and further comprising the step of: reinitiating the delivery of electrical energy if the heart should fail to be cardioverted after a delivery of energy.

10. The method of claim 1, wherein said second electrode is located outside the heart, within the vascular system.

11. In a system for cardioverting a malfunctioning heart, comprising storage means for storing electrical energy, sensing means for sensing heart malfunction susceptible to conversion by electrical shock, electrode means for electrically connecting the storage means to the heart, and means for initiating the discharge of the electrical energy stored by said storage means across said electrode means and into the heart upon sensing a malfunction: a single intravascular cardioverting catheter carrying said electrode means in the form of first and second electrodes for contacting the tissues of the heart so as to cardiovert the same upon discharge of said storage means, said first and second electrodes being spaced apart a distance of at least about two and one-half inches; and connecting means for connecting said first and second electrodes across said storage means.

12. The catheter of claim 11, wherein said first electrode comprises at least two conductive surfaces spaced apart from one another; wherein said second electrode is spaced apart from said first electrode by at least a distance greater than the spacing between each of said first electrode conductive surfaces; wherein said second electrode comprises at least two conductive surfaces spaced apart from one another; and further comprising: first connecting means for electrically connecting all of said conductive surfaces of said first electrode in series and adapted to be electrically connected to a first side of said storage means; and second connecting means for electrically connecting all of said conductive surfaces of said second electrode in series and adapted to be electrically connected to a second side of said storage means different in potential from said first side.

13. The catheter of claim 12, and further comprising: sealing means for providing electrical insulation and for maintaining the spacing between said conductive surfaces of said first electrode, between said first and second electrode and between said conductive surfaces of said second electrode and providing electrical insulation around and between said first and second connecting means.

14. The catheter of claim 12, wherein said conductive surfaces of said first and second electrodes are rings.

15. The catheter of claim 11, wherein the closest spacing between said first and second electrodes is between 3 and 5 inches.

16. The catheter of claim 15, wherein the closest spacing between said first and second electrodes is between 4 and 4½ inches.

17. The catheter of claim 11, wherein the closest spacing between said first and second electrodes is between 2½ and 4 inches.

18. The catheter of claim 11, wherein said catheter is of a flexible material to accommodate safe application through the vascular system.

19. The catheter of claim 11, wherein said system for cardioverting a malfunctioning heart further comprises conventional pacemaking electronics; and further comprising connection means for associating with said conventional pacemaking electronics.

20. The catheter of claim 11, wherein said sensing means comprises a pressure sensitive bulb located near one end of said catheter for sensing blood pressure.

21. The catheter of claim 11, and further comprising: means for sealing said connecting means so as to be inert to body fluids.

22. The catheter of claim 11, wherein said first electrode is adapted to be wedged into the apex of the right ventricle and said second electrode is adapted to be positioned immediately superior to the right atrium just outside the heart in the vascular system.

23. The catheter of claim 11, wherein said system for cardioverting a malfunctioning heart further comprises a conventional heart pacer; and further comprising: a pacing tip carried by said catheter at the very end thereof; and means for connecting said tip to said heart pacer; whereby said catheter is adapted to function both in a cardioverting mode and a pacemaking mode.

24. A system for cardioverting a malfunctioning heart, the system comprising: storage means for storing electrical energy; a single intravascular cardioverting catheter carrying spaced first and second electrode means connected across said storage means for connecting the storage means directly to the heart and contacting the tissues of the heart for cardioverting the heart upon discharge of said storage means, said first and second electrode means being spaced apart a distance of at least 2½ inches; and means for switching said storage means into a discharge state, whereupon the stored energy is released and applied directly to the heart across said first and second electrode means.

25. The system as recited in claim 24, wherein one of said electrode means is adapted to be positioned within the heart cavity to be cardioverted, and the other of said electrode means is adapted to be positioned outside the heart.

26. The system as set forth in claim 24, and further comprising conventional pacemaking electronics for developing electrical pacing impulses; and means for connecting said pacemaking electronics to said single intravascular catheter.

27. The system as set forth in claim 24, wherein: said first electrode means carried by said catheter is near one end thereof and is adapted to be positioned within the heart; and said second electrode means carried by said catheter is adapted to be positioned outside the heart within the vascular system when said catheter is located in operative position.

28. The system as set forth in claim 24, wherein: said first electrode means carried by said catheter is located near one end of said catheter and comprises a plurality of conductive surfaces spaced apart from one another; said second electrode means carried by said catheter is spaced from said first electrode means by a distance greater than the spacings between each of said first electrode conductive surfaces, and comprises a plurality of conductive surfaces spaced apart from one another; and further comprising connector means for electrically connecting in series all of said conductive surfaces of said first electrode means; connector means for electrically connecting in series all of said conductive surfaces of said second electrode means; means for attaching the respective connector means across said storage means; and means for maintaining the spacing between said conductive surfaces of said first electrode means, between said first and second electrode means, and between said conductive surfaces of said second electrode means and for providing electrical insulation around and between the respective connector means.

29. A system for automatically cardioverting a malfunctioning heart, the system comprising: storage means for storing electrical energy; a single intravascular cardioverting catheter carrying sensing means for continually sensing the function of a heart, and at least two spaced electrodes for connecting the storage means directly to the heart and for contacting the tissues of the heart so as to cardiovert the heart upon discharge of said storage means, said spaced electrodes being separated by a distance of at least approximately 2½ inches; discriminator means electrically in circuit with said sensing means and electrodes for discriminating between normal heart function and an arrhythmia correctable by cardioversion; and means for automatically switching said storage means into a discharge state, in response to a sensed arrhythmia correctable by cardioversion, whereupon the stored energy is applied directly to the heart through said electrodes to cardiovert the malfunctioning heart.

30. The system as set forth in claim 29, and further comprising: delay means for ensuring that a time delay exists between the sensing of the initial heart malfunction and the discharge of said storage means into the heart.

31. The system as set forth in claim 29, wherein said sensing means and at least one of said electrodes are adapted to be positioned within the heart.

32. The system as set forth in claim 29, wherein said switching means further comprises means for reinitiating the heart-shocking cycle if the heart should fail to be cardioverted after being shocked.

33. The system as set forth in claim 29, wherein said switching means inhibits the discharge of said storage means under conditions of normal heart activity.

34. The system as set forth in claim 29 wherein said catheter carries one of said electrodes near one end thereof and adapted to be positioned within the heart, and the other of said electrodes spaced from the first and adapted to be positioned outside the heart within the vascular system when said catheter is located in operative position.

35. The system as set forth in claim 29, wherein said single intravascular catheter comprises: a pressure sensitive bulb included in said sensing means and located near one end of said catheter for sensing blood pressure; the first of said electrodes carried by said catheter adjacent said bulb, said first electrode comprising a plurality of conductive surfaces, spaced apart from one another; the second of said electrodes spaced from said first electrode a distance greater than the spacings between each of said first electrode conductive surfaces, said second electrode comprising a plurality of conductive surfaces, spaced apart from one another; first means for electrically connecting all of said surfaces of said first electrode in series, said first means being adapted to be electrically connected to said storage means; second means for electrically connecting all of said surfaces of said second electrode in series, said second means being adapted to be electrically connected to said storage means; and means for maintaining the spacing between said conductive surfaces of said first electrode, between said first and second electrodes, and between said conductive surfaces of said second electrode and for providing electrical insulation around and between said first and second means.

36. A system for cardioverting a malfunctioning heart, the system comprising: an energy source for developing cardioverting electrical energy; storage means connected to said energy source for storing said electrical energy; a single intravascular cardioverting catheter carrying first and second spaced electrodes for connecting the storage means directly to the heart and contacting the tissues of the heart to cardiovert the same upon discharge of said storage means, said first electrode being fixed on said catheter at a first location and connected to one terminal of said storage means, said second electrode being electrically isolated from said first electrode, fixed on said catheter at a second location and connected to an opposite terminal of said storage means, said first electrode adapted to be positioned within the heart and said second electrode adapted to be positioned outside the heart; and means for switching said storage means into a discharge state, whereby the stored energy is released from said storage means and applied directly to the heart through said first and second electrodes to cardiovert the malfunctioning heart.

37. A system for automatically cardioverting a malfunctioning heart, the system comprising: an energy source for developing cardioverting electrical energy; storage means connected to said energy source for storing said electrical energy; a single intravascular cardioverting catheter carrying sensing means and at least first and second spaced electrodes for continually sensing the function of a heart, for connecting the storage means directly to the heart, and for contacting the tissues of the heart to cardiovert the same upon discharge of said storage means, said first of said electrodes being fixed on said catheter at a first location and connected to one terminal of said storage means, said second of said electrodes being electrically isolated from said first, fixed on said catheter at a second location and connected to an opposite terminal of said storage means, said first electrode adapted to be positioned within the heart and said second electrode adapted to be positioned outside the heart; discriminator means electrically in circuit with said sensing means and electrodes for receiving information from said sensing means indicative of heart function, and for discriminating between normal heart function and an arrhythmia correctable by cardioversion; and means for automatically switching said storage means into a discharge state, in response to a sensed arrhythmia correctable by cardioversion, whereupon the stored energy is applied directly to the heart through said electrodes to cardiovert the malfunctioning heart.

38. For use in a system for cardioverting a malfunctioning heart, an energy source for developing cardioverting electrical energy, a storage means connected to the energy source for storing the electrical energy until needed, first and second spaced electrodes connected across the storage means, and means for switching the storage means into a discharge state whereby the stored energy is released and applied directly to the heart through the first and second spaced electrodes to cardiovert the malfunctioning heart, the improvement comprising: a single intravascular cardioverting catheter carrying the first and second spaced electrodes for connecting the storage means directly to the heart and contacting the tissues of the heart to cardiovert the same upon discharge of said storage means, said first electrode being fixed on the catheter at a first location and connected to one terminal of said storage means, and said second electrode being fixed on the catheter at a second location spaced from the first and connected to an opposite terminal of said storage means, one of said electrodes adapted to be positioned within the heart chamber to be cardioverted and the other of said electrodes adapted to be positioned outside said heart chamber.

39. The catheter of claim 38, wherein said first and second electrodes are spaced apart a distance of at least 2½ inches.

40. A system for cardioverting a malfunctioning heart, the system comprising: storage means for storing electrical energy of at least approximately 0.1 watt-seconds; sensing means for sensing heart malfunction susceptible to cardioversion by electrical shock; a single intravascular cardioverting catheter carrying first and second electrodes spaced apart a distance of at least about 2½ inches; means for connecting said first and second electrodes across said storage means; and switching means for responding to heart malfunctions sensed by said sensing means by discharging the energy stored by said storage means across said first and second electrodes and into said malfunctioning heart.

41. The system of claim 40, wherein said first and second electrodes are spaced apart on said cardioverting catheter by an intermediate catheter body of flexible material.

42. The system of claim 40, wherein said first and second electrodes are elongated and are flexible along their respective lengths.

* * * * *

REEXAMINATION CERTIFICATE (653rd)
United States Patent [19]
Mirowski et al.

[11] B1 3,942,536
[45] Certificate Issued Mar. 24, 1987

[54] CARDIOVERTING DEVICE HAVING SINGLE INTRAVASCULAR CATHETER ELECTRODE SYSTEM AND METHOD FOR ITS USE

[75] Inventors: Mieczyslaw Mirowski, Rte. 3, Velvet Valley Way, Owings Mills, Md. 21117; Morton M. Mower, Baltimore, Md.; Rollin H. Denniston, III, Anoka, Minn.

[73] Assignee: Mieczyslaw Mirowski, Owings Mills, Md.

Reexamination Request:
No. 90/000,917, Dec. 6, 1985

Reexamination Certificate for:
Patent No.: 3,942,536
Issued: Mar. 9, 1976
Appl. No.: 398,793
Filed: Sep. 19, 1973

Related U.S. Application Data

[63] Continuation-in-part of Ser. No. 124,326, Mar. 15, 1971, abandoned.

[51] Int. Cl.[4] .......................... A61N 1/36; A61N 1/04; A61B 5/04
[52] U.S. Cl. ............................... 128/419 D; 128/642; 128/786
[58] Field of Search ..................... 128/419 D, 784, 786

[56] References Cited
U.S. PATENT DOCUMENTS

| | | |
|---|---|---|
| 164,184 | 6/1875 | Kidder ................................ 128/418 |
| 3,348,548 | 10/1967 | Chardack . |
| 3,472,234 | 10/1969 | Tachick ............................... 128/418 |
| 3,614,954 | 10/1971 | Mirowski et al. ............... 128/419 D |
| 3,729,008 | 4/1973 | Berkovits . |
| 3,738,370 | 6/1973 | Charms .......................... 128/419 D |
| 3,804,098 | 4/1974 | Friedman . |
| 3,815,611 | 6/1974 | Denniston, III . |
| 3,825,015 | 7/1974 | Berkovits . |
| 3,857,398 | 12/1974 | Rubin . |
| 4,030,509 | 6/1977 | Heilman et al. ................ 128/419 D |

OTHER PUBLICATIONS

Mower et al, "Ventricular Defibrillation with a Single Intravascular Catheter System Having Distal Electrode in Left Pulmonary Artery and Proximal Electrode in Right Ventricle or Right Atrium", Clinical Research, vol. 20, No. 3, Apr. 1972, p. 389.

Mirowski et al, "Standby Automatic Defibrillator", Arch Int. Med., 126: 158-161, (7/70).

Mirowski, M., "Heart Disease Toll Seen Cut by Automatic Defibrillation", Int. Med. News, 5:1 (1/72).

Mirowski et al, "The Development of the Transvenous Automatic Defibrillator", Arch Int. Med., 129: 773-79 (May 1972).

Schuder et al, "Experimental Ventricular Defibrillator With an Automatic and Completely Implanted System", Trans ASAIO, XVI: 207-12 (4/70).

Schuder et al, "Ventricular Defibrillation Using Bipolar Catheter and Truncated Exponential Stimuli", 24th ACEMB, 6.4 (11/71).

Gould, S. E., Pathology of the Heart and Blood Vessels, Chas. Thomas, 3rd, ed., pp. 91-93, (1968).

Parsonnet et al, "The Development of an Intracardiac Dipolar Catheter Electrode for the Treatment of Complete Heart Block", Surgical Forum, 13: 179-80.

Hopps et al, "Electrical Treatment of Cardiac Arrest: A Cardiac Stimulator-Defibrillator", Surgery 36:833-849 (1954).

Rogel et al, "The Universal Pacer", J. Thor. Card. Surg., 61(3): 466-71 (1971).

Moore et al, "Preferred Cardiac Axis for Electrical Stimulation", Bull. School Med., Univ. Maryland, 52(1): 3-5 (1967).

Eckner et al, "Dimensions of Normal Human Hearts", Arch. Path., vol. 88, 11/69, pp. 497-507.

Kushner et al, "The American Journal of Cardiology" vol. 42, Nov. 1978, pp. 733-737.

*Primary Examiner*—William E. Kamm

[57] ABSTRACT

Apparatus and method for either manually or automatically initiating the cardioversion of a malfunctioning heart. The apparatus includes a single intravascular catheter electrode system which allows for a much more compact cardioverting system capable of being completely implanted within the patient. The heart function is continuously monitored, and when the function becomes abnormal, the malfunctioning heart is shocked by a voltage of sufficient amplitude to restore the heart to normalcy. If the heart does not return to its normal functions after a given interval, then it is again shocked. Normal heart activity ensures that the shocking mechanism remains inert.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–10 is confirmed.

Claim 12 is cancelled.

Claims 11, 13, 14, 16, 24, 29, 36–38, and 40 are determined to be patentable as amended.

Claims 15, 17–23, 25–28, 30–35, 39, 41 and 42, dependent on an amended claim, are determined to be patentable.

11. In a system for cardioverting a malfunctioning heart, comprising storage means for storing electrical energy, sensing means for sensing heart malfunction susceptible to conversion by electrical shock, electrode means for electrically connecting the storage means to the heart, and means for initiating the discharge of the electrical energy stored by said storage means across said electrode means and into the heart upon sensing a malfunction: a single intravascular cardioverting catheter carrying said electrode means in the form of first and second electrodes for contacting the tissues of the heart so as to cardiovert the same upon discharge of said storage means, said first and second electrodes being spaced apart a distance of at least about two and one-half inches; and connecting means for connecting said first and second electrodes across said storage means *wherein said first electrode comprises at least two conductive surfaces spaced apart from one another; wherein said second electrode is spaced apart from said first electrode by at least a distance greater than the spacing between each of said first electrode conductive surfaces; wherein said second electrode comprises at least two conductive surfaces spaced apart from one another; and further comprising: first connecting means for electrically connecting all of said conductive surfaces of said first electrode in series for electrically connecting to a first side of said storage means; and second connecting means for electrically connecting all of said conductive surfaces of said second electrode in series for electrically connecting to a second side of said storage means different in potential from said first side.*

13. The catheter of claim [12] *11*, and further comprising: sealing means for providing electrical insulation and for maintaining the spacing between said conductive surfaces of said first electrode, between said first and second electrode and between said conductive surfaces of said second electrode and providing electrical insulation around and between said first and second connecting means.

14. The catheter of claim [12] *11*, wherein said conductive surfaces of said first and second electrodes are rings.

16. [The catheter of claim 15,] *In a system for cardioverting a malfunctioning heart, comprising storage means for storing electrical energy, sensing means for sensing heart malfunction susceptible to conversion by electrical shock, electrode means for electrically connecting the storage means to the heart, and means for initiating the discharge of the electrical energy stored by said storage means across said electrode means and into the heart upon sensing a malfunction: a single intravascular cardioverting catheter carrying said electrode means in the form of first and second electrodes for contacting the tissues of the heart so as to cardiovert the same upon discharge of said storage means* wherein the closest spacing between said first and second electrodes is between 4 and 4½ inches; *and connecting means for connecting said first and second electrodes across said storage means.*

24. A system for cardioverting a malfunctioning heart, the system comprising: storage means for storing electrical energy; a single intravascular cardioverting cathether carrying spaced first and second electrode means connected across said storage means for connecting the storage means directly to the heart and contacting the tissues of the heart for cardioverting the heart upon discharge of said storage means, said first and second electrode means being spaced apart a distance of [at least 2½] *between about 4 and 4½* inches; and means for switching said storage means into a discharge state, whereupon the stored energy is released and applied directly to the heart across said first and second electrode means.

29. A system for automatically cardioverting a malfunctioning heart, the system comprising: storage means for storing electrical energy; a single intravascular cardioverting catheter carrying sensing means for continually sensing the function of a heart, and at least two spaced electrodes for connecting the storage means directly to the heart for contacting the tissues of the heart so as to cardiovert the heart upon discharge of said storage means, said spaced electrodes being separated *for positioning one electrode at the apex of the right ventricle of the heart and for positioning the other electrode immediately superior to the right atrium of the heart* [by a distance of at least approximately 2½ inches]; discriminator means electrically in circuit with said sensing means and electrodes for discriminating between normal heart function and an arrhythmia correctable by cardioversion; and means for automatically switching said storage means into a discharge state, in response to a sensed arrhythmia correctable by cardioversion, whereupon the stored energy is applied directly to the heart through said electrode to cardiovert the malfunctioning heart.

36. A system for cardioverting a malfunctioning heart, the system comprising: an energy source for developing cardioverting electrical energy; storage means connected to said energy source for storing said electrical energy; a single intravascular cardioverting catheter carrying first and second spaced electrodes for connecting the storage means directly to the heart and contacting the tissues of the heart to cardiovert the same upon discharge of said storage means, said first electrode being fixed on said catheter at a first location *for positioning at the apex of the right ventricle of the heart*, and connected to one terminal of said storage means, said second electrode being electrically isolated from said first electrode, fixed on said catheter at a second location *for positioning immediately superior to the right atrium of the heart*, and connected to an opposite terminal of said storage means, said first electrode adapted to be positioned within the heart and said second electrode adapted to be positioned outside the heart; and means for switching said storage means into a discharge state, whereby the stored energy is released from said storage means and applied directly to the heart through said first and second electrodes to cardiovert the malfunctioning heart.

37. A system for automatically cardioverting a malfunctioning heart, the system comprising: an energy source for developing cardioverting electrical energy; storage means connected to said energy source for storing said electrical energy; a single intravascular cardioverting catheter carrying sensing means and at least first and second spaced electrodes for continually sensing the function of a heart, for connecting the storage means directly to the heart, and for contacting the tissues of the heart to cardiovert the same upon discharge of said storage means, said first of said electrodes being fixed on said catheter at a first location *for positioning at the apex of the right ventricle of the heart*, and connected to one terminal of said storage means, said second of said electrodes being electrically isolated from said first, fixed on said catheter at a second location *for positioning immediately superior to the right atrium of the heart*, and connected to an opposite terminal of said storage means, said first electrode adapted to be positioned within the heart and said second electrode adapted to be positioned outside the heart; discriminator means electrically in circuit with said sensing means and electrodes for receiving information from said sensing means indicative of heart function, and for discriminating between normal heart function and an arrhythmia correctable by cardioversion; and means for automatically switching said storage means into a discharge state, in response to a sensed arrhythmia correctable by cardioversion, whereupon the stored energy is applied directly to the heart through said electrodes to cardiovert the malfunctioning heart.

38. For use in a system for cardioverting a malfunctioning heart, an energy source for developing cardioverting electrical energy, a storage means connected to the energy source for storing the electrical energy until needed, first and second spaced electrodes connected across the storage means, and means for switching the storage means into a discharge state whereby the stored energy is released and applied directly to the heart through the first and second spaced electrodes to cardiovert the malfunctioning heart, the improvement comprising: a single intravascular cardioverting catheter carrying the first and second spaced electrodes for connecting the storage means directly to the heart and contacting the tissues of the heart to cardiovert the same upon discharge of said storage means, said first electrode being fixed on the catheter at a first location and connected to one terminal of said storage means, and said second electrode being fixed on the catheter at a second location spaced from the first and connected to an opposite terminal of said storage means, one of said electrodes adapted to be positioned within the heart chamber to be cardioverted and the other of said electrodes adapted to be positioned outside said heart chamber *wherein said first electrode comprises at least two conductive surfaces spaced apart from one another; wherein said second electrode is spaced apart from said first electrode by at least a distance greater than the spacing between each of said first electrode conductive surfaces; wherein said second electrode comprises at least two conductive surfaces spaced apart from one another; and further comprising first connecting means for electrically connecting all of said conductive surfaces of said first electrode in series for electrically connecting to said one terminal of said storage means; and second connecting means for electrically connecting all of said conductive surfaces of said second electrode in series for electrically connecting to said opposite terminal of said storage means different in potential from said first terminal.*

40. A system for cardioverting a malfunctioning heart, the system comprising: storage means for storing electrical energy of at least approximately 0.1 watt-seconds; sensing means for sensing heart malfunction susceptible to cardioversion by electrical shock; a single intravascular cardioverting catheter carrying first and second electrodes spaced apart a distance of at least about 2½ inches; means for connecting said first and second electrodes across said storage means; and switching means for responding to heart malfunctions sensed by said sensing means by discharging the energy stored by said storage means across said first and second electrodes and into said malfunctioning heart *wherein said first electrode comprises at least two conductive surfaces spaced apart from one another; wherein said second electrode is spaced apart from said first electrode by at least a distance greater than the spacing between each of said first electrode conductive surfaces; wherein said second electrode comprises at least two conductive surfaces spaced apart from one another; and further comprising: first connecting means for electrically connecting all of said conductive surfaces of said first electrode in series for electrically connecting to a first side of said storage means; and second connecting means for electrically connecting all of said conductive surfaces of said second electrode in series for electrically connecting to a second side of said storage means different in potential from said first side.*

* * * * *